United States Patent
Amber et al.

(10) Patent No.: US 6,790,040 B2
(45) Date of Patent: Sep. 14, 2004

(54) HEALING COMPONENTS FOR USE IN TAKING IMPRESSIONS AND METHODS FOR MAKING THE SAME

(75) Inventors: John T. Amber, Jupiter, FL (US); Stephan S. Porter, Palm Beach Gardens, FL (US); Theodore M. Powell, Jupiter, FL (US)

(73) Assignee: Implant Innovations, Inc., Palm Beach Gardens, FL (US)

( * ) Notice: Subject to any disclaimer, the term of this patent is extended or adjusted under 35 U.S.C. 154(b) by 169 days.

(21) Appl. No.: 10/007,997

(22) Filed: Nov. 13, 2001

(65) Prior Publication Data

US 2002/0039717 A1 Apr. 4, 2002

Related U.S. Application Data

(63) Continuation-in-part of application No. 09/710,208, filed on Nov. 10, 2000, now Pat. No. 6,558,162.
(60) Provisional application No. 60/164,521, filed on Nov. 10, 1999.

(51) Int. Cl.[7] ................................................ A61C 8/00
(52) U.S. Cl. ........................................ 433/173; 433/213
(58) Field of Search ................................. 433/173, 172, 433/174, 213, 214

(56) References Cited

U.S. PATENT DOCUMENTS

| 3,958,471 A | 5/1976 | Müller |
| 4,011,602 A | 3/1977 | Rybicki et al. |
| 4,086,701 A | 5/1978 | Kawahara et al. |
| 4,177,562 A | 12/1979 | Miller et al. |
| 4,306,862 A | 12/1981 | Knox |
| 4,341,312 A | 7/1982 | Scholer |
| 4,547,157 A | 10/1985 | Driskell |
| 4,615,678 A | * 10/1986 | Moermann et al. ...... 433/201.1 |
| 4,624,673 A | 11/1986 | Meyer |
| 4,713,004 A | 12/1987 | Linkow et al. |
| 4,758,161 A | 7/1988 | Niznick |
| 4,767,331 A | 8/1988 | Hoe |
| 4,772,204 A | 9/1988 | Söderberg |
| 4,842,518 A | 6/1989 | Linkow et al. |
| 4,850,870 A | 7/1989 | Lazzara et al. |
| 4,850,873 A | 7/1989 | Lazzara et al. |
| 4,854,872 A | 8/1989 | Detsch |

(List continued on next page.)

FOREIGN PATENT DOCUMENTS

| DE | 21 14 323 | 10/1971 | |
| DE | 35 31 389 A1 | 3/1987 | |
| DE | 40 28 855 A1 | 3/1992 | |
| EP | 0 442 855 A1 | 8/1991 | |
| EP | 0 583 829 A1 | 2/1994 | ............ A61C/8/00 |
| EP | 0 657 146 A1 | 6/1995 | |
| EP | 0 727 193 A1 | 8/1996 | |
| EP | 0 747 017 A2 | 12/1996 | |
| FR | 2 759 896 | 8/1998 | |
| GB | 1 291 470 | 10/1972 | ............ A61F/1/00 |
| WO | WO 85/02337 | 6/1985 | ............ A61C/8/00 |
| WO | WO 01/34057 A1 | 5/2001 | ............ A61C/8/00 |

OTHER PUBLICATIONS

"The Basics of Bar Coding" Zebra Technologies Corporation, Vernon Hills, IL 60061 USA.*

(List continued on next page.)

*Primary Examiner*—Ralph A. Lewis
(74) *Attorney, Agent, or Firm*—Jenkens & Gilchrist

(57) ABSTRACT

The present invention provides a healing abutment for attachment to a dental implant with marking locations thereon. The marking locations either lack or have markers that provide a binary code system for retrieving unique information about the healing abutment and the underlying implant.

31 Claims, 12 Drawing Sheets

U.S. PATENT DOCUMENTS

| | | |
|---|---|---|
| 4,856,994 A | 8/1989 | Lazzara et al. |
| 4,872,839 A | 10/1989 | Brajnovic |
| 4,906,191 A | 3/1990 | Soderberg |
| 4,955,811 A | 9/1990 | Lazzara et al. |
| 4,988,297 A | 1/1991 | Lazzara et al. |
| 4,988,298 A | 1/1991 | Lazzara et al. |
| 5,000,685 A | 3/1991 | Brajnovic |
| 5,006,069 A | 4/1991 | Lazzara et al. |
| 5,015,186 A | 5/1991 | Detsch |
| 5,030,096 A | 7/1991 | Hurson et al. |
| 5,035,619 A | 7/1991 | Daftary |
| 5,040,983 A | 8/1991 | Binon |
| 5,064,375 A | 11/1991 | Jörnéus |
| 5,071,351 A | 12/1991 | Green, Jr. et al. |
| 5,073,111 A | 12/1991 | Daftary |
| 5,100,323 A | 3/1992 | Friedman et al. |
| 5,104,318 A | 4/1992 | Piche et al. |
| 5,106,300 A | 4/1992 | Voitik |
| 5,122,059 A | 6/1992 | Dürr et al. |
| 5,125,839 A | 6/1992 | Ingber et al. |
| 5,125,841 A | 6/1992 | Carlsson et al. |
| 5,135,395 A | 8/1992 | Marlin |
| 5,145,371 A | 9/1992 | Jörnéus |
| 5,145,372 A | 9/1992 | Daftary et al. |
| 5,188,800 A | 2/1993 | Green, Jr. et al. |
| 5,195,892 A | 3/1993 | Gersberg |
| 5,205,745 A | 4/1993 | Kamiya et al. |
| 5,209,659 A | 5/1993 | Friedman et al. |
| 5,209,666 A | 5/1993 | Balfour et al. |
| 5,213,502 A | 5/1993 | Daftary |
| 5,246,370 A | 9/1993 | Coatoam |
| 5,281,140 A | 1/1994 | Niznick |
| 5,286,195 A | 2/1994 | Clostermann |
| 5,292,252 A | 3/1994 | Nickerson et al. |
| 5,297,963 A | 3/1994 | Daftary |
| 5,312,254 A | 5/1994 | Rosenlicht |
| 5,316,476 A | 5/1994 | Krauser |
| 5,322,436 A | 6/1994 | Horng et al. |
| 5,334,024 A | 8/1994 | Niznick |
| 5,336,090 A | 8/1994 | Wilson, Jr. et al. |
| 5,338,196 A | 8/1994 | Beaty et al. |
| 5,338,198 A | 8/1994 | Wu et al. |
| 5,344,457 A | 9/1994 | Pilliar et al. |
| 5,362,234 A | 11/1994 | Salazar et al. |
| 5,362,235 A | 11/1994 | Daftary |
| 5,368,483 A | 11/1994 | Sutter et al. |
| 5,417,570 A | 5/1995 | Zuest et al. |
| 5,419,702 A | 5/1995 | Beaty et al. |
| 5,431,567 A | 7/1995 | Daftary |
| 5,437,551 A | 8/1995 | Chalifoux |
| 5,452,219 A | 9/1995 | Dehoff et al. |
| 5,458,488 A | 10/1995 | Chalifoux |
| 5,476,382 A | 12/1995 | Daftary |
| 5,476,383 A | 12/1995 | Beaty et al. |
| 5,492,471 A | 2/1996 | Singer |
| 5,527,182 A | 6/1996 | Willoughby |
| 5,533,898 A | 7/1996 | Mena |
| 5,538,426 A | 7/1996 | Harding et al. |
| 5,547,377 A | 8/1996 | Daftary |
| 5,564,921 A | 10/1996 | Marlin |
| 5,564,924 A | 10/1996 | Kwan |
| 5,651,675 A | 7/1997 | Singer |
| 5,658,147 A | 8/1997 | Phimmasone |
| 5,662,476 A | 9/1997 | Ingber et al. |
| 5,674,069 A | 10/1997 | Osorio |
| 5,674,071 A | 10/1997 | Beaty et al. |
| 5,674,073 A | 10/1997 | Ingber et al. |
| 5,681,167 A | 10/1997 | Lazarof |
| 5,685,715 A | 11/1997 | Beaty et al. |
| 5,733,123 A | 3/1998 | Blacklock et al. |
| 5,759,036 A | 6/1998 | Hinds |
| 5,810,592 A | 9/1998 | Daftary |
| 5,813,858 A | 9/1998 | Singer |
| 5,846,079 A | 12/1998 | Knode |
| 5,851,115 A | 12/1998 | Carlsson et al. |
| 5,857,853 A | 1/1999 | Van Nifterick et al. |
| 5,871,358 A | 2/1999 | Ingber et al. |
| 5,873,722 A | 2/1999 | Lazzara et al. |
| 5,938,443 A | 8/1999 | Lazzara et al. |
| 5,964,591 A | 10/1999 | Beaty et al. |
| 6,093,023 A | 7/2000 | Sala Meseguer ............ 433/173 |
| 6,120,293 A | 9/2000 | Lazzara et al. |
| 6,129,548 A | 10/2000 | Lazzara et al. |
| 6,135,773 A | 10/2000 | Lazzara |
| 6,257,890 B1 | 7/2001 | Khoury et al. |
| 6,273,720 B1 | 8/2001 | Spalten |
| 6,312,260 B1 | 11/2001 | Kumar et al. |
| 6,406,295 B1 | 6/2002 | Mahler ....................... 433/173 |
| 6,558,162 B1 * | 5/2003 | Porter et al. ................. 433/173 |

OTHER PUBLICATIONS

Exhibit A, drawing of a healing abutment, 1 page (no date).

Exhibit B, assembly drawing of a coping and the conponent drawings which comprise the coping assembly, 3 pages (1989, 1990, 1991).

Exhibit C, drawing of one piece healing abutment (made of DERLIN™).

Adell, R., et al., "A 15–Year Study Of Osseointegrated Implants In The Treatment Of The Edentulous Jaw," *Int. J. Oral Surg.*, vol. 10, pp. 387–416 (1981).

Core–Vent® Corporation, "1989 Core–Vent Implant Symposium" Brochure, 2 pages (Mar. 1988).

Impla–Med™ Incorporated, "Come To The Source. The Choice Is Clear." Catalog, 16 pages (Mar. 1991).

Impla–Med, Inc., and Dental Imaging Associates, Inc., "The DIA Anatomic Abutment System™" Brochure, 12 pages (Oct. 1991).

Imtec Corporation, "Hexed–Head™ Implant System" Catalog, 16 pages (Spring 1993).

Lazzara, Richard J., "Managing The Soft Tissue Margin: The Key To Implant Aesthetics," *Practical Periodontics And Aesthetic Denistry*, vol. 5, No. 5, pp. cover, 81–87 (Jun./Jul. 1993).

Lewis, Steven G., et al., "Single Tooth Implant Supported Restorations," *The International Journal of Oral & Maxillofacial Implants*, vol. 3, No. 1, pp. 25–30 (1988).

Lewis, S., et al., "The 'UCLA' Abutment," *The International Journal of Oral & Maxillofacial Implants*, vol. 3, No. 3, pp. 183–189 (1988).

Oratronics Inc., "Endosseous Tri–Dimensional T–3D Oral Implant Healing System (OIHS)" Brochure, 8 pages (1978).

Perri, George, et al., "Single Tooth Implants," *Journal of the California Dental Association*, vol. 17, No. 3, pp. cover, 30–33 (Mar. 1989).

Prosthetics, "EsthetiCone™ System Components" Catalog, 1 page (1991).

Steri–Oss Inc., Bio–Esthetic™ Technique Manual, 6 pages (1995).

Steri–Oss Inc., "Osstium" Brochure, 8 pages (Fall 1995).

Stryker, Price List, 46 pages (Jun. 1, 1993).

Stryker, "Surgical Flexibility Prosthetic Simplicity" Brochure, 8 pages (no date).

* cited by examiner

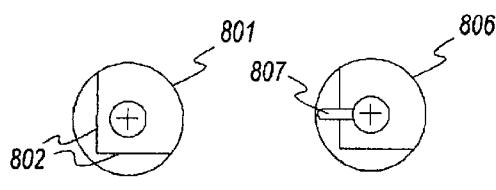
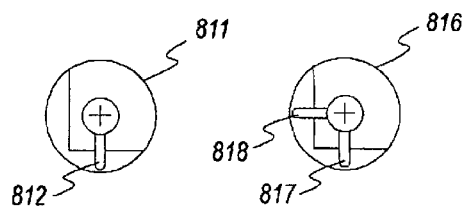
FIG. 9a  FIG. 9b  FIG. 9c  FIG. 9d
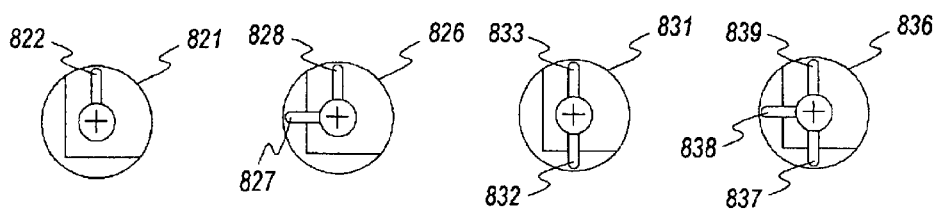
FIG. 9e  FIG. 9f  FIG. 9g  FIG. 9h
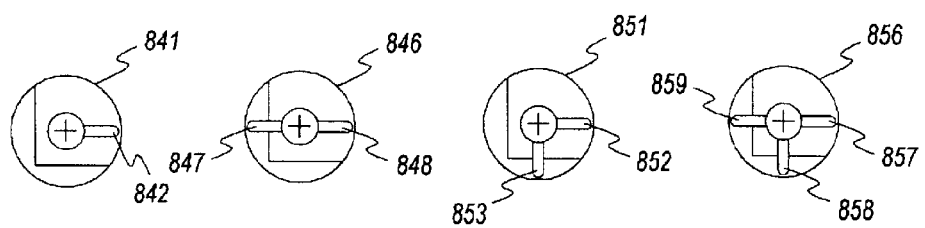
FIG. 9i  FIG. 9j  FIG. 9k  FIG. 9l
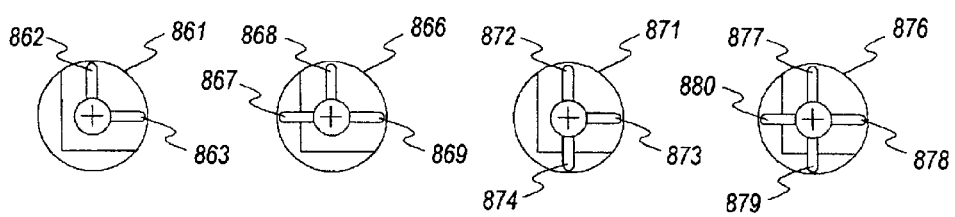
FIG. 9m  FIG. 9n  FIG. 9o  FIG. 9p

HEALING COMPONENTS FOR USE IN TAKING IMPRESSIONS AND METHODS FOR MAKING THE SAME

CROSS-REFERENCE TO RELATED APPLICATIONS

This is a continuation-in-part application of U.S. patent application Ser. No. 09/710,208, filed Nov. 10, 2000, now U.S. Pat. No. 6,558,162 which claimed the benefit of priority of U.S. Patent Application No. 60/164,521, filed Nov. 10, 1999.

TECHNICAL FIELD OF INVENTION

The present invention relates generally to a healing abutment in a dental implant system. More particularly, the present invention relates to the use of a binary marking system on the exterior of a healing abutment to identify unique characteristics of the healing abutment.

BACKGROUND OF THE INVENTION

The dental restoration of a partially or wholly edentulous patient with artificial dentition is typically done in two stages. In the first stage, an incision is made through the gingiva to expose the underlying bone. An artificial tooth root, usually a dental implant, is placed in the jawbone for integration. The dental implant generally includes a threaded bore to receive a retaining screw holding mating components therein. During the first stage, the gum tissue overlying the implant is sutured and heals as the osseointegration process continues.

Once the osseointegration process is complete, the second stage is initiated. Here, the gum tissue is re-opened to expose the end of the dental implant. A healing component or healing abutment is fastened to the exposed end of the dental implant to allow the gum tissue to heal therearound. Preferably, the gum tissue heals such that the aperture that remains generally approximates the size and contour of the aperture that existed around the natural tooth that is being replaced. To accomplish this, the healing abutment attached to the exposed end of the dental implant has the same general contour as the gingival portion of the natural tooth being replaced. It should be noted that the healing abutment can be placed on the implant immediately after the implant has been installed and before osseointegration.

During the typical second stage of dental restoration, the healing abutment is removed and an impression coping is fitted onto the exposed end of the implant. This allows an impression of the specific region of the patient's mouth to be taken so that an artificial tooth is accurately constructed. Thus, in typical dental implant systems, the healing component and the impression coping are two physically separate components. Preferably, the impression coping has the same gingival dimensions as the healing component so that there is no gap between the impression coping and the wall of the gum tissue defining the aperture. Otherwise, a less than accurate impression of the condition of the patient's mouth is taken. The impression coping may be a "pick-up"-type impression coping or a "transfer"-type impression coping, both known in the art. After these second stage processes, a dental laboratory creates a prosthesis to be permanently secured to the dental implant from the impression that was made.

In addition to the method that uses the impression material and mold to manually develop a prosthesis, systems exist that utilize scanning technology to assist in generating a prosthesis. A scanning device is used in one of at least three different approaches. First, a scanning device can scan the region in the patient's mouth where the prosthesis is to be placed without the need to use impression materials or to construct a mold. Second, the impression material that is removed from the healing abutment and the surrounding area is scanned to produce the permanent components. Third, a dentist can scan the stone model of the dental region that was formed from the impression material or scan the stone model.

Three basic scanning techniques exist: laser scanning, photographic imaging, and mechanical sensing. Each scanning technique is used or modified for any of the above-listed approaches (a scan of the stone model, a scan of the impression material, or a scan in the mouth without using impression material) to create the prosthesis. After scanning, a laboratory can create and manufacture the permanent crown or bridge, usually using a computer-aided design ("CAD") package.

The utilization of a CAD program, as disclosed in U.S. Pat. No. 5,338,198 (Wu), whose disclosure is incorporated herein by reference, is one method of scanning a dental region to create a three-dimensional model. Preferably, after the impression is taken of the patient's mouth, the impression material or stone model is placed on a support table defining the X-Y plane. A scanning laser light probe is directed onto the model. The laser light probe emits a pulse of laser light that is reflected by the model. A detector receives light scattered from the impact of the beam with the impression to calculate a Z-axis measurement. The model and the beam are relatively translated within the X-Y plane to gather a plurality of contact points with known locations in the X-Y coordinate plane. The locations of several contact points in the Z-plane are determined by detecting reflected light. Finally, correlating data of the X-Y coordinates and the Z-direction contact points creates a digital image. Once a pass is complete, the model may be tilted to raise one side of the mold relative to the opposite vertically away from the X-Y plane. Subsequent to the model's second scan, the model may be further rotated to allow for a more accurate reading of the model. After all scans are complete, the data may be fed into a CAD system for manipulation of this electronic data by known means.

Photographic imaging can also be used to scan impression material, a stone model, or directly in the mouth. For example, one system takes photographs at multiple angles in one exposure to scan a dental region, create a model, and manufacture a prosthetic tooth. As disclosed in U.S. Pat. No. 5,851,115 (Carlsson), whose disclosure is incorporated herein by reference, this process is generally initiated with the process of taking a stereophotograph with a camera from approximately 50 to 150 mm away from the patient's mouth. The stereophotograph can involve a photograph of a patient's mouth already prepared with implantation devices. Correct spatial positioning of the dental implants is obtained by marking the implant in several locations. The resulting photograph presents multiple images of the same object. The images on the photographs are scanned with a reading device that digitizes the photographs to produce a digital image of the dental region. The data from the scanner is electronically transmitted to a graphical imaging program that creates a model that is displayed to the user. After identification of the shape, position, and other details of the model, the ultimate step is the transmission of the data to a computer for manufacturing.

A third scanning measure uses mechanical sensing. A mechanical contour sensing device, as disclosed in U.S. Pat.

No. 5,652,709 (Andersson), whose disclosure is incorporated herein by reference, is another method used to read a dental model and produce a prosthetic tooth. The impression model is secured to a table that may rotate about its longitudinal axis as well as translate along the same axis with variable speeds. A mechanical sensing unit is placed in contact with the model at a known angle and the sensing equipment is held firmly against the surface of the model by a spring. When the model is rotated and translated, the sensing equipment can measure the changes in the contour and create an electronic representation of the data. A computer then processes the electronic representation and the data from the scanning device to create a data array. The computer further compresses the data for storage and/or transmission to the milling equipment.

SUMMARY OF THE INVENTION

The present invention is a healing abutment having a plurality of external marking locations where markers are either present or absent. Due to the presence or absence of the markers, the physical characteristics of the healing abutment are identifiable through use of a binary-coded system. The present invention contemplates providing a set of healing abutments, each of which has unique physical characteristics and a unique binary marking code that indicates those unique physical characteristics.

During the first or second stage of dental restoration, a healing abutment is non-rotationally fastened to the implant through complimentary non-round fittings on the implant and abutment, which usually take the form of a hexagonal boss and socket. The healing abutment is held on the implant via a screw that engages the threaded bore of the implant.

According to the invention, the presence or absence of the markers in the marking locations may eliminate the need for an impression coping within the implant system. An impression can be taken of the mouth with the markers creating features in the impression material. The impression or a model of the impression is read or scanned such that the markers indicate various characteristics of the healing abutment and also the implant. Further, such a system eliminates the need to remove the healing abutment until the permanent components are ready to be installed in the patient's mouth.

Specifically, the presence or absence of the binary-coded markers in the marking locations allow the dentist to determine various physical characteristics, such as the healing abutment height, healing abutment diameter, dimensions of the attached implant seating surface, and the orientation of the implant's fitting. It is contemplated in accordance with one embodiment of the present invention that these marking locations containing the binary-coded markers are preferably located on the top of the healing abutment, although it may be possible to place some markers on the side of the healing abutment.

In other embodiments of the present invention not using this binary-coded system, the information markers correspond to the height of the abutment to be captured in an impression or subsequent scan. For example, a 6 mm tall healing abutment may possess six information markers on the top or side surface of the healing abutment. A 4 mm tall healing abutment may possess four information markers, and a 2 mm tall healing abutment may possess two information markers. This marking system may be altered to decrease the quantity of information markers required on the top or side surface of the healing abutment. For example, it is contemplated in accordance with the present invention that the use of three information markers on the top or side surface may represent a 6 mm tall healing abutment, two information markers may represent a 4 mm tall healing abutment, and one marker may represent a 2 mm tall healing abutment.

It is also contemplated that the healing abutments of the present invention can be manufactured in sets of healing abutments, each set having healing abutments of the same diameter but different healing abutment heights. Different sets of healing abutments would have healing abutments with different diameters. For example, a first set of healing abutments may contain three healing abutments, one abutment of 2 mm, 4 mm, and 6 mm height, respectively, and each with a diameter of 4 mm. A second set of healing abutments may also have abutments with heights of 2 mm, 4 mm, and 6 mm, but these abutments may have a diameter of 5 mm. Information markers at one or more marking locations distinguish not only between the first and second set of healing abutments, but also between the three healing abutments within each set.

An impression of the mouth is taken with the inventive healing abutment mounted on the implant. The impression process creates a "negative" image of the information markers in the impression material that change the physical shape of the top or side surface. A corresponding mold is created from the impression. This mold, or a stone model created from the mold, can then be scanned. A computer program is able to create a three-dimensional perspective of the relevant jaw section of the patient, including the implant and abutment. Due to the information markers on the surface of the healing abutment now present in the mold, the computer program is able to accurately analyze and produce the appropriate dimensions of the aperture in the gingiva and the orientation of the underlying hexagonal boss of the implant so that a clinician can instruct a milling machine to produce the permanent components.

In an alternative embodiment, the scanner simply takes the necessary information directly from the mouth of a patient without the need for impression material whatsoever. The information markers of the healing abutment provide the required information of the gingival aperture and the orientation of the underlying hexagonal boss on the implant. If a laser or photographic scanning system is used, the etched markers are identified just as easily as the markers that change the physical shape of the healing abutment.

This system allows the dentist to produce the permanent components more quickly because the healing abutment does not have to be removed in order to produce the permanent dental components. In other words, the second step of taking an impression with an impression coping is eliminated. The dentist also does not have to confront the difficulties of gingival closure that appear when a healing implant is removed. Finally, the patient is not forced to endure the somewhat painful procedure of healing abutment removal. With the procedure of the present invention, the removal of the healing abutment can occur during the same surgery as the installation of the permanent components.

In a further alternative embodiment, it is contemplated in accordance with the present invention that an impression coping may possess information markers as described above and replace the standard healing abutment during second stage dental restoration surgery. The impression coping and surrounding environment are scanned directly in the mouth. An impression could also be formed and a stone model produced from the impression. This stone model is scanned to create the permanent prosthesis using one of the scanning techniques described above.

BRIEF DESCRIPTION OF THE DRAWINGS

The foregoing and other advantages of the invention will become apparent upon reading the following detailed description and upon reference to the drawings.

FIG. 1b is a longitudinal cross-sectional view of the healing abutment shown in FIG. 1a.

FIG. 2b is a longitudinal cross-sectional view of the healing abutment shown in FIG. 2a.

FIG. 3b is a longitudinal cross-sectional view of the healing abutment shown in FIG. 3a.

FIG. 4b is a longitudinal cross-sectional view of the healing abutment shown in FIG. 4a.

FIG. 5b is a longitudinal cross-sectional view of the healing abutment shown in FIG. 5a.

FIG. 6b is a longitudinal cross-sectional view of the healing abutment shown in FIG. 6a.

FIGS. 9a–9p are top views of a plurality of healing abutments having a binary-type system of information markers.

Figure 1B:
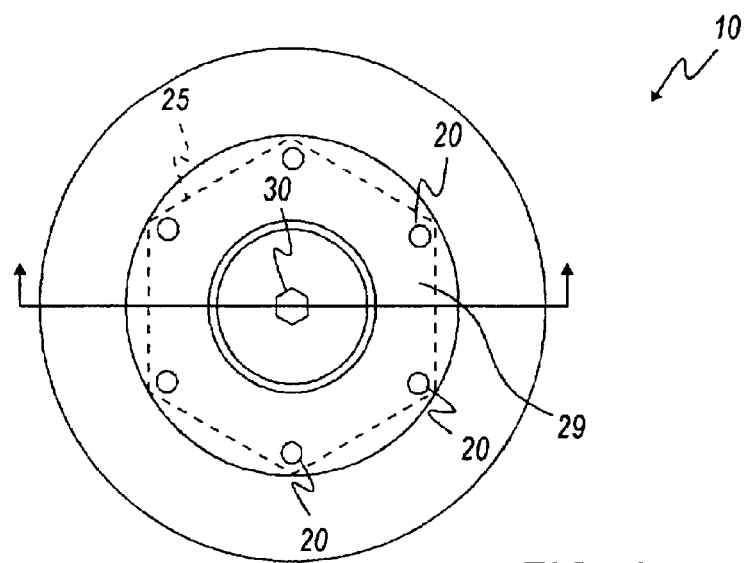

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DESCRIPTION OF ILLUSTRATIVE EMBODIMENTS

Figure 1A:
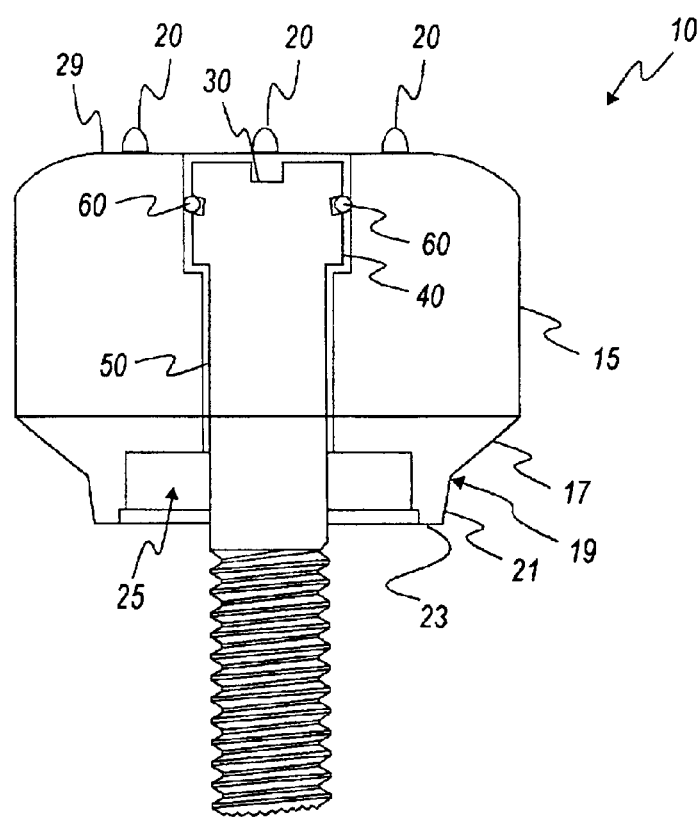
FIG. 1a is a top view of a healing abutment.

As shown in FIGS. 1a and 1b, the healing abutment 10 of one embodiment of the present invention has a main body 15 with a generally circular cross-sectional shape, a first tapered section 17, a boundary 19, a second tapered section 21, an end surface 23, a hex socket 25, and dimensions that are generally suitable for replicating the emergence profile of a natural tooth. The first tapered section 17 extends downward from the main body 15 of the abutment 10, having a diameter at a boundary 19 that is generally larger than the implant (not shown). The boundary 19 separates the first tapered section 17 from the second tapered section 21 that terminates in the end surface 23. The second tapered section 21 is at an angle with the central axis of the implant that is generally in the range of from about 5° to about 15°, with 10° being preferable. Alternatively, the second tapered section 21 may be omitted such that the first tapered section 17 tapers directly to the diameter of the end surface 23 of the implant. In a further embodiment, the first tapered section 17 may merge smoothly into the second tapered section 21, without the distinct boundary 19 separating the two tapered sections 17, 21. The hexagonal orientation socket or hex 25 is for mating with a hexagonal boss on the implant. The end surface 23 has generally the same diameter as the seating surface of the implant.

FIG. 1b discloses the top view of the same healing abutment 10 shown in FIG. 1a. As shown in FIGS. 1a and 1b, the healing abutment 10 has positive information markers 20 protruding from a top surface 29 of the healing abutment 10. Each of the six positive information markers 20 is disposed such that it aligns with the six corners of the underlying hex 25. It is also contemplated in accordance with the present invention that the six information markers 20 may also correspond to the height of the healing abutment. For example, two information markers may correspond to a 2 mm tall healing abutment and four information markers may correspond to a 4 mm tall healing abutment. In these embodiments, the two or four information markers would still be at the corners of the underlying hex 25 so that the relative position of the hex is known.

Figure 1C:
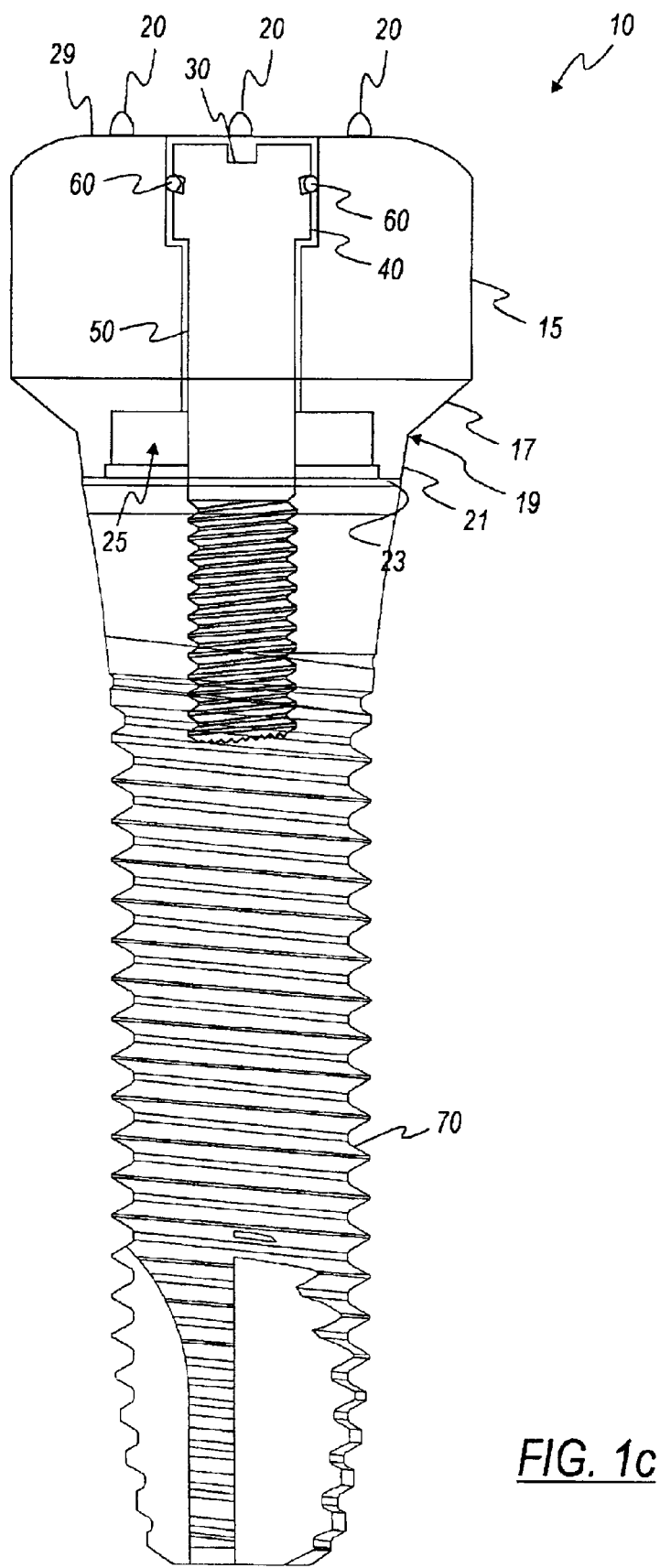
FIG. 1c is the healing abutment shown in FIG. 1b attached to an implant.

A socket 30 on the exposed surface of a head portion 40 of an attaching bolt 50 is shaped to accept a wrench (not shown) for turning the attaching bolt 50 into the threaded bore of an implant 70, as shown in FIG. 1c. It is contemplated in accordance with the present invention that each of the healing abutments described herein and shown in the figures can be secured to an implant by means of an attaching bolt, as is known in the art. An O-ring 60 carried on the head portion 40 of the attaching bolt 50 fills an annular gap left between the head and the entrance section near the outermost (widest) opening in the entrance section.

Figure 2B:
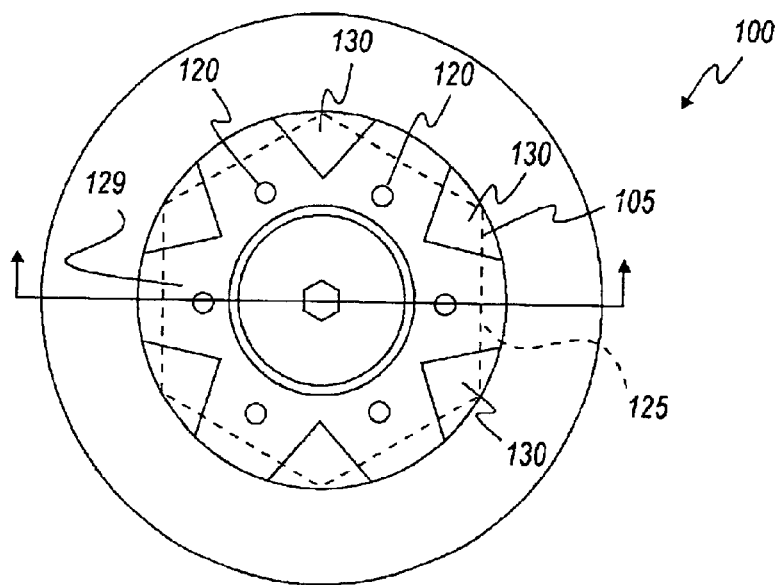
Figure 2A:
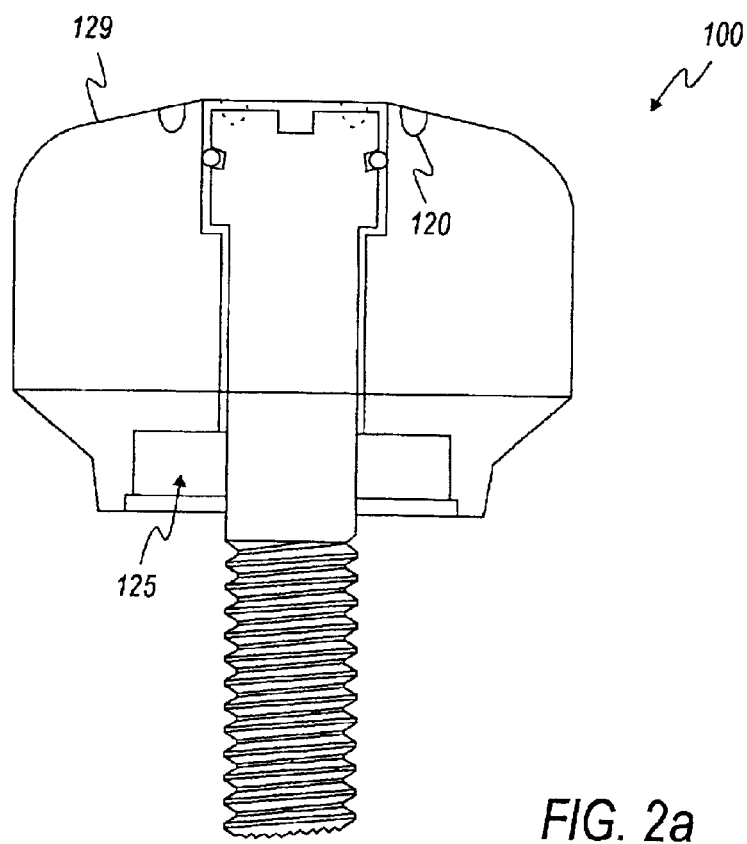
FIG. 2a is a top view of another embodiment of a healing abutment.

A healing abutment 100 of FIG. 2a comprises many of the same features as the healing abutment 10 shown in FIG. 1a. Dashed lines 125 in FIG. 2b correspond to the underlying hex 125 of the healing abutment 100 in FIG. 2a. A top surface 129 includes negative information markers (recesses) 120 that are displayed in FIG. 2a as dimples extending below the top surface 129 of the healing abutment 100. The top surface 129 of the healing abutment 100 also possesses six notches 130 that are machined into the corners. The top surface 129 is generally flat and merges into a rounded shape at the periphery of the healing abutment 100.

The notches 130 are used, for example, to determine the identification of the underlying implant hex position 125, the height of the healing abutment, or the diameter of the healing abutment. This embodiment is not limited to comprising six notches in the top surface 129 of the healing abutment 100. It is also contemplated that one embodiment of the present invention may possess four notches or even two notches for indicative purposes. Furthermore, it is contemplated that the information marker and notch approach could be combined or modified to provide information regarding the underlying implant seating surface diameter and implant hex angulation.

Figure 3B:
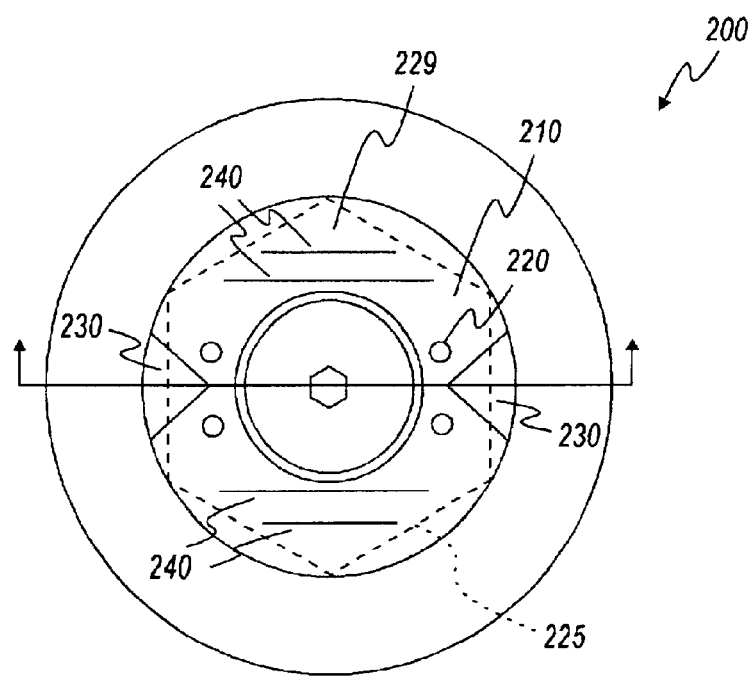
Figure 3A:
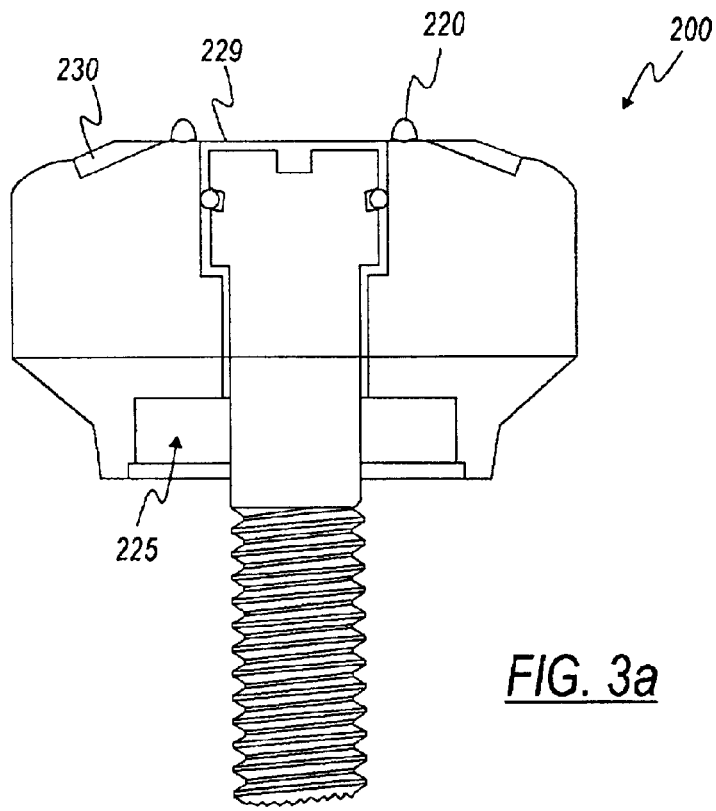
FIG. 3a is a top view of yet another embodiment of a healing abutment.

In another embodiment of the present invention, a healing abutment 200 shown in FIGS. 3a and 3b displays four positive information markers 220 shown to, for example, indicate a 4 mm tall healing abutment 200. It is contemplated that the number of information markers 220 could decrease or increase depending on the height of the healing abutment 200 or another variable that the information markers have been designated to correspond. The positive information markers 220 also define a corresponding one of the six flat surfaces of an underlying hex 225. Furthermore, dashed lines 225 in FIG. 3b correspond directly to the underlying hex 225.

Two notches 230 have also been etched or machined onto a top surface 229 of the healing abutment of FIG. 3b. These notches may indicate the diameter of the implant's seating surface. Lines 240 are scribed on the top surface 229 of the healing abutment 200. The lines 240 are used to provide positioning or other information to the dentist or laboratory. Here, the lines 240 indicate the diameter of the healing abutment (e.g., 4 mm). In summary, the number of the positive information markers 220 indicates the height of the healing abutment 200. The position of the positive information markers 220 indicates the orientation of the hex 225 that is the orientation of the hexagonal boss on the implant. The notches 230 indicate the diameter of the seating surface of the implant. The lines 240 indicate the diameter of the healing abutment 200.

Figure 4B:
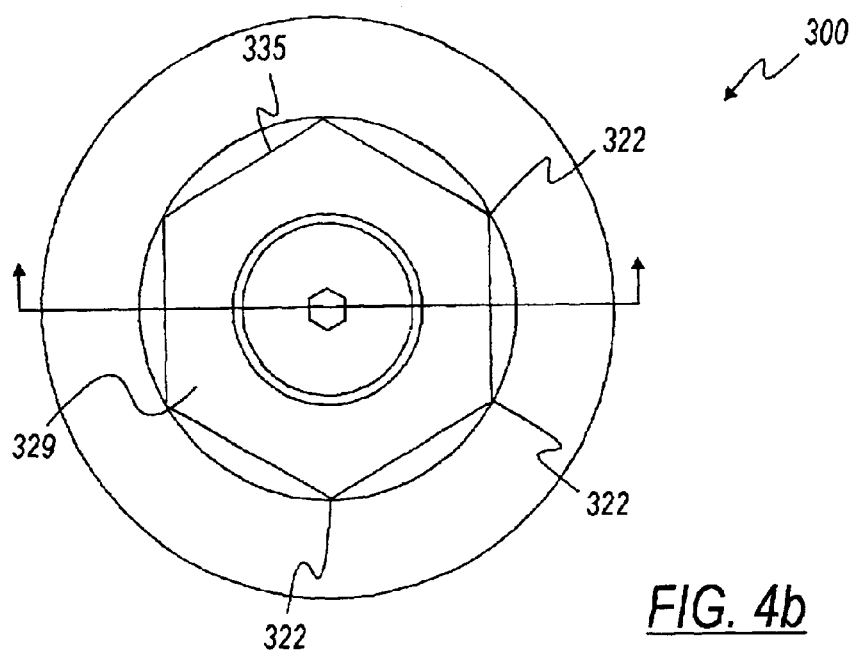
Figure 4A:
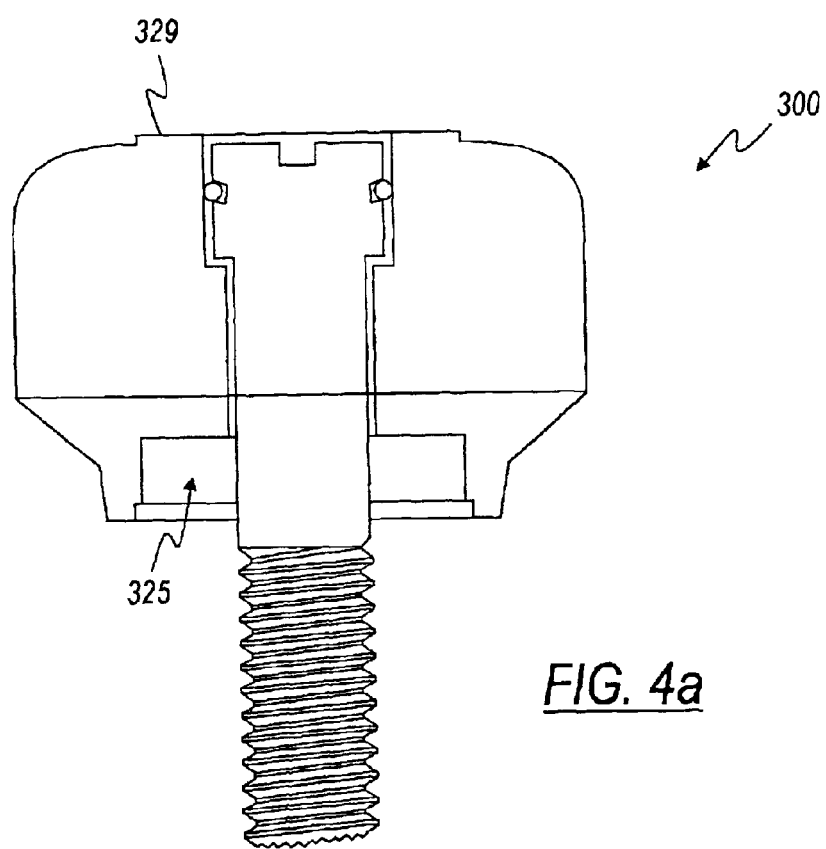
FIG. 4a is a top view of a further embodiment of the healing abutment.

In yet another embodiment of the present invention, a top surface 329 of the healing abutment 300 of FIGS. 4a and 4b comprises an etched or machined hex 335. Corners 322 of the etched hex 335 correspond directly to the position of the corners of an underlying hex 325 shown in FIG. 4a. It is contemplated in accordance with one embodiment of the present invention that further information markers may be added to the healing abutment for the dentist or laboratory to ascertain different heights or diameters.

Figure 5B:
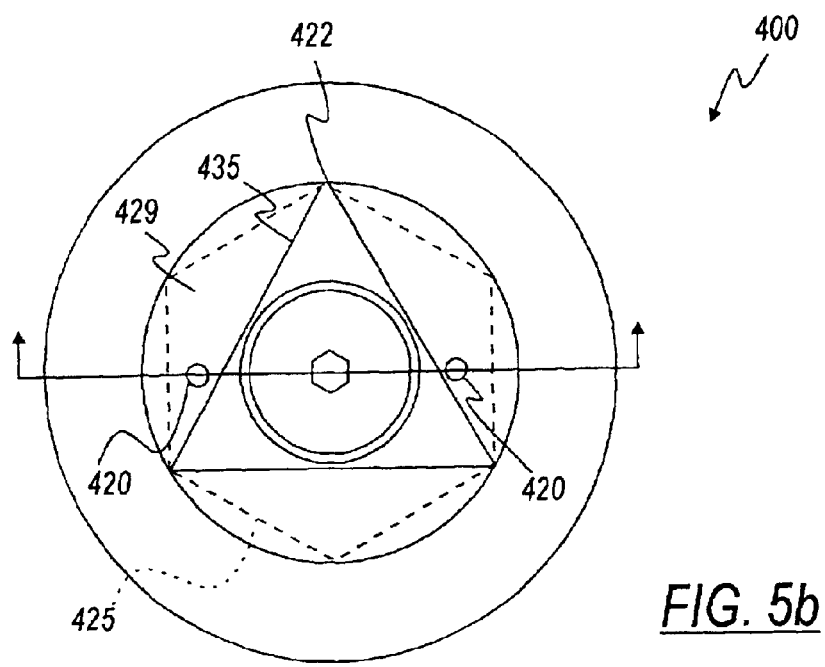
Figure 5A:
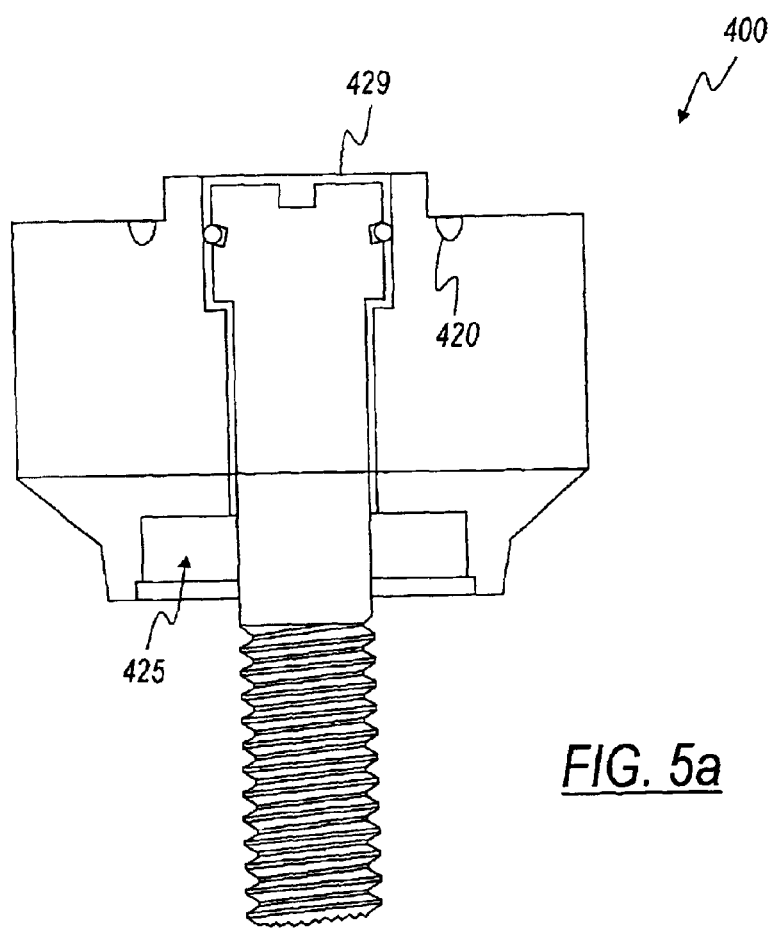
FIG. 5a is a top view of another embodiment of a healing abutment.

A top surface 429 of a healing abutment 400 shown in FIGS. 5a and 5b contains an etched or machined triangle 435. Dashed lines 425 in FIG. 5b indicate the location of an underlying hex 425. Corners 422 of the etched triangle 435 correspond to three of the six corners of the underlying hex 425. Furthermore, two negative information markers 420 are shown in FIG. 5b. As above, it is contemplated in accordance with the present invention that fewer than six information markers may exist to account for differing heights or diameters of the healing abutments.

Figure 6B:
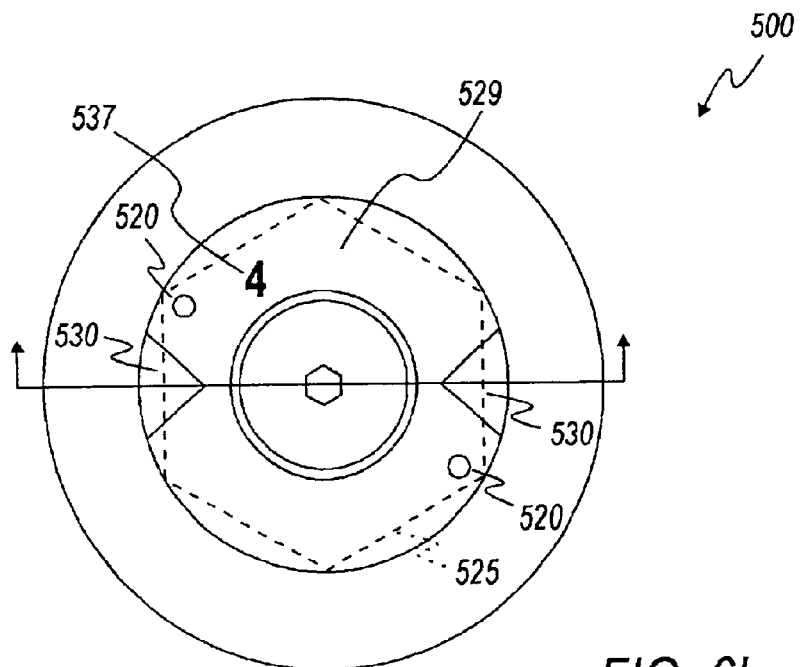
Figure 6A:
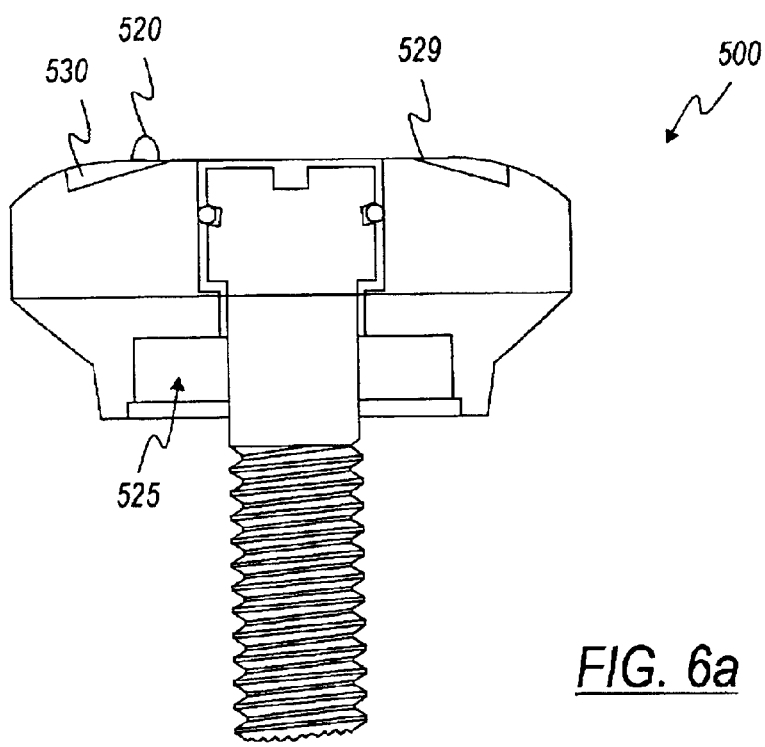
FIG. 6a is a top view of another embodiment of a healing abutment.

Another embodiment of the present invention is shown in FIGS. 6a and 6b. The healing abutment 500 displayed in FIGS. 6a and 6b is a shorter version of the healing abutment 10 shown in FIGS. 1a and 1b. Two positive information markers 520 are shown in FIG. 6b to identify the height of the healing abutment 500. Dashed lines 525 of the healing abutment 500 correspond with the location and orientation of the underlying hex 525. Two notches 530 are also shown in a top surface 529 of this embodiment of the present invention to show the orientation of two of the underlying flats of the underlying hex 525. A numeral "4" at 537 is located on the top surface 529 of the healing abutment 500 to indicate, for example, the diameter of the healing abutment 500. As shown, the numeral "4" at 537 corresponds to a healing abutment 500 with a diameter of 4 mm. It is contemplated in accordance with the present invention that other numerals could be placed on the top surface 529 of the healing abutment 500 to indicate other healing abutment diameters. Further, it is also contemplated that the numeral could represent the height of the healing abutment or the diameter of the underlying implant.

During the second stage of the prosthetic implementation process and after a healing abutment with the information markers has been placed, an impression of the mouth is made with only the healing abutments as described herein and without the use of an impression coping. A model of the impression is poured with, for example, die stone. Since the information markers are disposed on the top and/or side of the healing abutment, the laboratory has all necessary information to define the gingival aperture, the implant size, and the orientation of the underlying hex. This enables the laboratory to quickly prepare the permanent components. The system of the present invention also allows the maintenance of the soft tissue surrounding the healing abutment where, in prior systems, the soft tissue would close once the healing abutment was removed. The system spares the patient the pain of removing the healing abutment.

Figure 8:
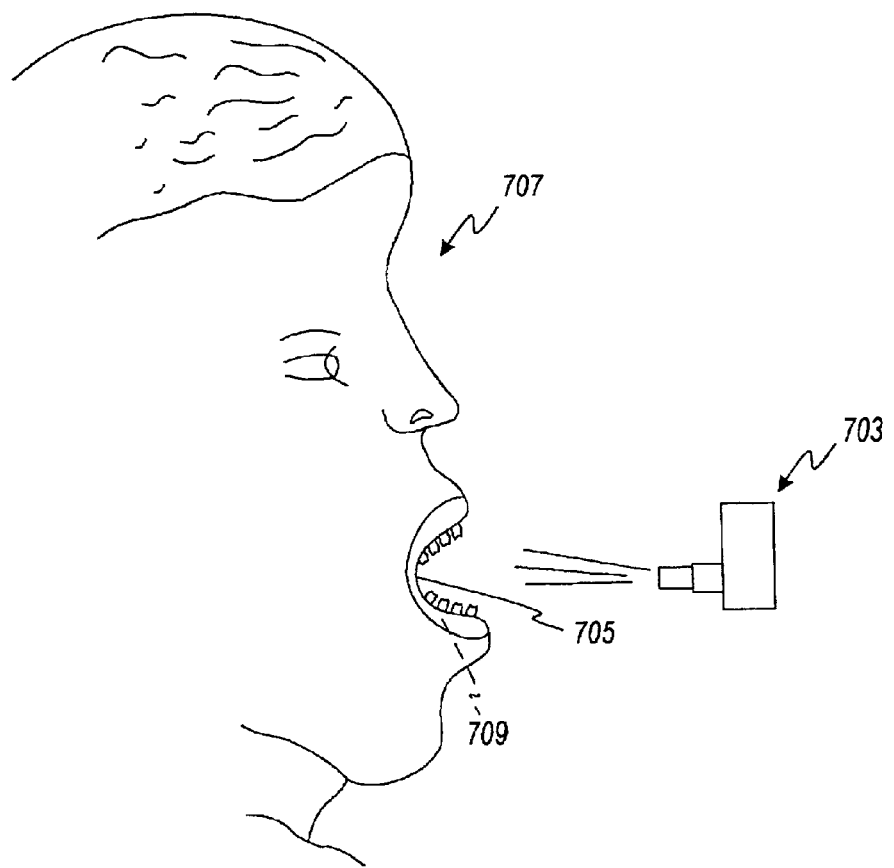
FIG. 8 is a side view of a method for stereophotographic imaging.

To create a permanent prosthesis, the dental region is scanned, as described above, from a stone model, from the impression material, or directly in the mouth using a laser scanning technique, a photographic scanning technique, or a mechanical sensing technique. FIG. 8 shows stereophotographic imaging, one method used for scanning. Stereophotography with a camera 703 is performed directly on the mouth cavity 705 of the patient 707. A clinician can photograph implants and other components that have been placed into or adjacent the patient's jawbone 709.

The scanned information is then transferred into a graphical imaging program for analysis. The graphical imaging software program, due to the information markers on the surface of the healing abutment, can perform a wide variety of functions. The graphical imaging program can scan an opposing cast in order to develop an opposing occlusal scheme and relate this information back to the primary model. This feature is extremely important because many clinical patients have implants in both maxillary and mandibular locations.

The graphical imaging software program is capable of generating a three-dimensional image of the emergence profile contours used on the healing abutment. If the implant is not placed in the desired esthetic location, the software program relocates the position of the restoration emergence through the soft tissue. The graphical imaging software program is also able to accurately relate the gingival margin for all mold, model, implant, and abutment dimensions. The software creates a transparent tooth outline for superimposition within the edentulous site. The occlusal outline of the "ghost" tooth should, if possible, be accurate and based on the scanned opposing occlusal dimensions. It is contemplated in accordance with the present invention that an occlusal outline is created by scanning a wax-up in order to maintain a proper plane of occlusion and healing abutment height.

The software program subtracts a given dimension from the mesial, distal, buccal, lingual, and occlusal areas of the superimposed tooth dimension. This allows for an even reduction of the healing abutment during fabrication for proper thickness of the overlying materials (e.g., gold, porcelain, targis, etc.). The graphical imaging software program also incorporates angulation measurements into the custom abutment and subsequently calculates the dimensions of the prosthesis that are checked and modified, if necessary, by a laboratory technician. Each of the features is analyzed and determined from the different information markers that exist on the healing abutments of the present invention.

The final dimensional information determined by the graphical imaging computer program is transferred from the computer to a milling machine (e.g., a 5 axis milling machine) to fabricate the custom abutment. It is contemplated in accordance with the present invention that the custom abutment can be fashioned from gold or titanium or other similar metals or composites. A custom milled coping can then be fabricated. It is contemplated in accordance with the present invention that the custom milled coping can be formed from titanium, plastic, gold, ceramic, or other similar metals and composites.

Figure 7:
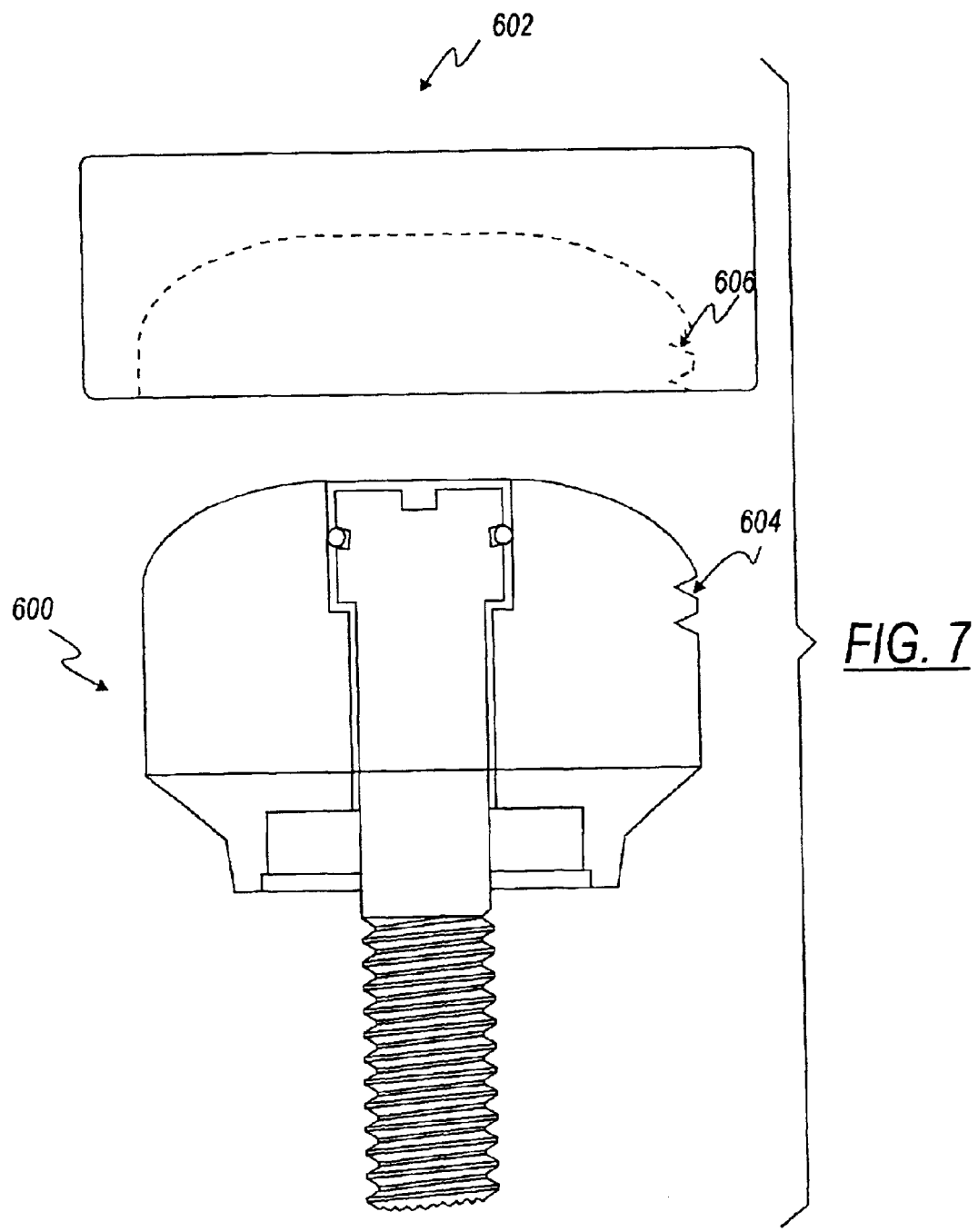
FIG. 7 is an exploded view of another embodiment of the present application.

FIG. 7 shows the exploded view of another embodiment of the present invention. A cap 602 is placed on a healing abutment 600 and later removed during the process of taking the impression of the healing implant and surrounding features of the patient's mouth. It is contemplated in accordance with the present invention that the cap 602 could be formed from plastic or metal or a composite material. As shown in FIG. 7, notches 604 are formed in the side(s) of the healing abutment 600. These notches correspond to notches 606 that have been preformed in the cap 602. When the cap 602 is placed on the healing abutment 600, the cap only fits snugly and properly if the number of notches 606 in the cap 602 correspond exactly to the number of notches 604 in the side wall(s) of the healing abutment. It is contemplated in accordance with the present invention that there could be many less or more notches than is depicted in FIG. 7. These notches correspond to information parameters such as healing abutment height, healing abutment, and/or implant diameter, and other parameters as listed above.

Specifically, after the healing abutment has been secured to the implant, the cap 602 is securely placed over the top of the healing abutment 600. The impression material is then placed over the top of the cap 602. The impression is then either scanned in the patient's mouth or the impression material (with the cap 602) is scanned and the process continues as described above.

FIGS. 9a–9p depict yet another embodiment of the present invention. Specifically, FIGS. 9a–9p show the top view of a plurality of healing abutments, each of which has four marking locations on the top surface of the healing abutment. For each healing abutment, a marker is either present or absent in each of the four marking locations, and the presence or absence can be interpreted either visually or by a scanning device. As explained below in detail, the markers in the marking locations permit identification of healing abutment characteristics, such as dimensions of the healing abutment.

In FIGS. 9a–9p, the four rows correspond to four different healing abutment heights (e.g., 3 mm, 4 mm, 6 mm, and 8 mm). The four columns of the coding key correspond to four different diameters of the healing abutment seating surfaces (e.g., 3.4 mm, 4.1 mm, 5.0 mm, and 6.0 mm). Accordingly, sixteen unique healing abutments are present.

The top surface of each of the healing abutments has from zero to four information markers located in the four marking locations. As shown in FIGS. 9a–9p, the marking locations extend radially from a central region of the healing abutment to the outer region of the top surface of the healing abutments (i.e., at locations of 12 o'clock, 3 o'clock, 6 o'clock, and 9 o'clock).

As is well known, a binary-coded system exists as an array of digits, where the digits are either "1" or "0" that represent two states, respectively, ON and OFF. For each marking location, the presence of a marker ("ON") is a 1 and the absence of a marker ("OFF") is a 0. By grouping sets of 1's and 0's together, information about each healing abutment is known. In the illustrative embodiment, the determination of the sets of 1's and 0's derived from the information markers (e.g., via visual inspection, scanning in the mouth, scanning of the impression, or scanning of the model created by the impression) provide information on the height of the healing abutment and the diameter of the seating surface of the attached implant.

The information markers shown in FIGS. 9a–9p are in the form of grooves having rounded cross-sections. The present invention, however, provides that the cross-section of these grooves can be rectangular, triangular, or various other shapes. When an impression is created from the healing abutment, the grooved marking locations produce a protruding "mound"-like element in the impression. This impression is then scanned so that identifying features regarding the healing abutment can be obtained. Alternatively, a model of the patient's mouth is created from the impression such that the markings are again grooves in the model that substantially replicate the grooves in the healing abutments. Of course, the markers could also be protrusions instead of grooves. Further, if the unique characteristics of the healing abutment are to be identified through scanning in the mouth or simply visual scanning by the clinician, then markers not producing features in impression material, such as etched or laser marking, may also be used.

Turning now to the specifics of each healing abutment, FIG. 9a illustrates a top view of a healing abutment 801 that includes orientation pick-ups 802. These orientation pick-ups 802 are also present in each of the healing abutments shown in FIGS. 9b–9p. The most counterclockwise of the orientation pick-ups 802 (i.e., the horizontal pick-up at the lower region of FIGS. 9a–9p) is always parallel to one flat of the implant hex, as viewed from the top of the healing abutment. As shown, the orientation pick-ups 802 are a pair of bevels on the sides of the healing abutments in FIGS. 9a–9p. Alternatively, the orientation pick-ups 802 can be grooves or protruding ridges, as well.

The orientation pick-ups 802 serve a second function in that they dictate which of the four marking locations is the first marking location. The other three marking locations are then read in clockwise order, proceeding from the most counterclockwise pick-up 802 to the other three marking locations on the top surface of the healing abutment. In other words, as illustrated in FIGS. 9a–9p, the information marker at 6 o'clock is the first digit in the binary code, the information marker at 9 o'clock is the second digit in the binary code, the information marker at 12 o'clock is the third digit in the binary code, and the information marker at 3 o'clock is the fourth digit in the binary code. In summary, the position of the orientation pick-ups 802 allows for the determination of the position of one of the hex flats of the healing abutment (and, likewise, one of the hex flats on the implant), and also the starting point to check for the presence or absence of information markers.

The results of a scan (computer or visual) of the four information markers on the healing abutment 801 produce no information markers at the four marking locations on the healing abutment 801 of FIG. 9a. Thus, the binary code for the healing abutment 801 is 0000, indicating that no grooved marker is present in any of the four predetermined positions. Since the coding key is preset (on a chart or in computer software), the binary code 0000 indicates that the healing abutment 801 is a resident of first row and first column of the matrix depicted by FIG. 9, having a height of 3 mm and a seating surface diameter of 3.4 mm. Thus, the three distinct pieces of information obtained from the top of the healing abutment allow the clinician or laboratory to know (i) the orientation of the hex of the implant, (ii) the height of the healing abutment (i.e., the location of the implant's seating surface below the healing abutment), and (iii) the seating surface diameter of the healing abutment (or the size of the implant's seating surface).

The healing abutment 806 in FIG. 9*b* possesses a binary code of 0100 because only one information marker 807 is present in the second marking location. Thus, it is understood from the binary code that the healing abutment 806 is 3 mm in height and has a seating surface diameter of 4.1 mm. The two healing abutments 811, 816 in FIGS. 9*c*, 9*d* have binary codes of 1000 and 1100, respectively. Healing abutment 811 has an information marker 812 in the first marking location, while healing abutment 816 has information markers 817, 818 in the first two locations. Thus, the unique characteristics of these two healing abutments are known.

The healing abutments 821, 826, 831, 836 shown in FIGS. 9*e*–9*h* and having heights of 4 mm, but with varying seating surface diameters, would be interpreted as having binary codes 0010, 0110, 1010, and 1110, respectively. Healing abutment 821 has one information marker 822 present in the third marking location, thus resulting in a binary code of 0010, which is indicative of a healing abutment height of 4 mm and a seating surface diameter of 3.4 mm. Similar analyses on healing abutment 826 with information markers 827, 828, healing abutment 831 with information markers 832, 833, and healing abutment 836 with information markers 837, 838, 839 allow determinations of the unique characteristics of these healing abutments.

The healing abutments 841, 846, 851, 856 shown in FIGS. 9*i*–9*l* and having heights of 6 mm, but with varying seating surface diameters, would be interpreted as having binary codes 0001, 0101, 1001, and 1101, respectively. Healing abutment 841 has one information marker 842 present in the fourth marking location, thus resulting in a binary code of 0001, which is indicative of a healing abutment height of 6 mm and a seating surface diameter of 3.4 mm. Similar analyses on healing abutment 846 with information markers 847, 848, healing abutment 851 with information markers 852, 853, and healing abutment 856 with information markers 857, 858, 859 allow determinations of the unique characteristics of these healing abutments.

The healing abutments 861, 866, 871, 876 shown in FIGS. 9*m*–9*p* and having heights of 8 mm, but with varying seating surface diameters, would be interpreted as having binary codes 0011, 0111, 1011, and 1111, respectively. Healing abutment 861 has two information markers 862, 863, which is indicative of a healing abutment height of 8 mm and a seating surface diameter of 3.4 mm. Similar analyses on healing abutment 866 with information markers 867, 868, 869, healing abutment 871 with information markers 872, 873, 874, and healing abutment 876 with information markers 877, 878, 879, 880 allow determinations of the unique characteristics of these healing abutments.

While the matrix of the sixteen healing abutments in FIGS. 9*a*–9*p* show four implant seating surface diameters and four heights, the matrix could include other physical characteristics of the healing abutment. For example, the maximum diameter of the healing abutment could be information obtainable through the binary-coded system. The type of fitting on the healing abutment and, thus, the implant (i.e., internal hex or external hex) could be provided. Information unrelated to the healing abutment, but related to only the implant, could be used. For example, the manufacturer of the implant could be noted. Or, information regarding the type of screw that mates with the internally thread bore of the implant could be provided.

Further, while FIGS. 9*a*–9*p* demonstrate the ability of the four digit, binary-coded system to provide two physical characteristics of the healing abutment, it could provide three or more physical characteristics. For example, two seating surface sizes, four heights, and two maximum diameters would provide sixteen unique healing abutments. If more information were needed, a fifth marking location could be added to provide the opportunity for displaying thirty-two physical characteristics of the healing abutments and/or implant. And, while one marking location has been shown with marker, it is possible to have two or more markers in each marking location. For example, one circumferential groove and one radial groove within one location could represent two digits of a binary system. Alternatively, having two widths possible for each groove could provide additional indicia representative of certain information about the healing abutment.

While the invention has been described with round healing abutments, healing abutments anatomically shaped like teeth can take advantage of the information markers. Thus, the set of healing abutments could include components shaped like the various teeth, and the information markers could provide the information regarding which tooth shape is present on the healing abutment. For example, a set may include four types of molar-shaped healing abutments, four types of bicuspid-shaped healing abutments, four types of incisor-shaped healing abutments and four types of round abutments. The four information marker locations on each component in the set provide the information to determine which one of the sixteen healing abutments is being used.

It is contemplated that the present invention also covers a set of eight unique healing abutments (as opposed to the sixteen shown) requiring only three marking locations. The computer software and/or the visual chart in this situation would identify these eight unique healing abutments through binary codes possessing three digits. The potential binary codes corresponding to an ON or OFF determination at the three marking locations are 000, 100, 010, 001, 110, 101, 011, and 111. Similarly, if the set has only four unique healing abutments, only two marking locations would be required on the healing abutments to determine features regarding the healing abutment and the attached dental implant. The potential binary codes in a four healing abutment matrix are 00, 10, 01, and 11.

After the top surface of a healing abutment (or the impression of the top surface, or the model of the impression of the top surface) is analyzed, the orientation of the hex is known from the location of the orientation pick-ups 802 and, via the binary code, the abutment height and the seating surface of the healing abutment is known. Other information regarding the healing abutment and the attached implant can also be determined by adding other markers of the type previously shown.

Figure 9Q:
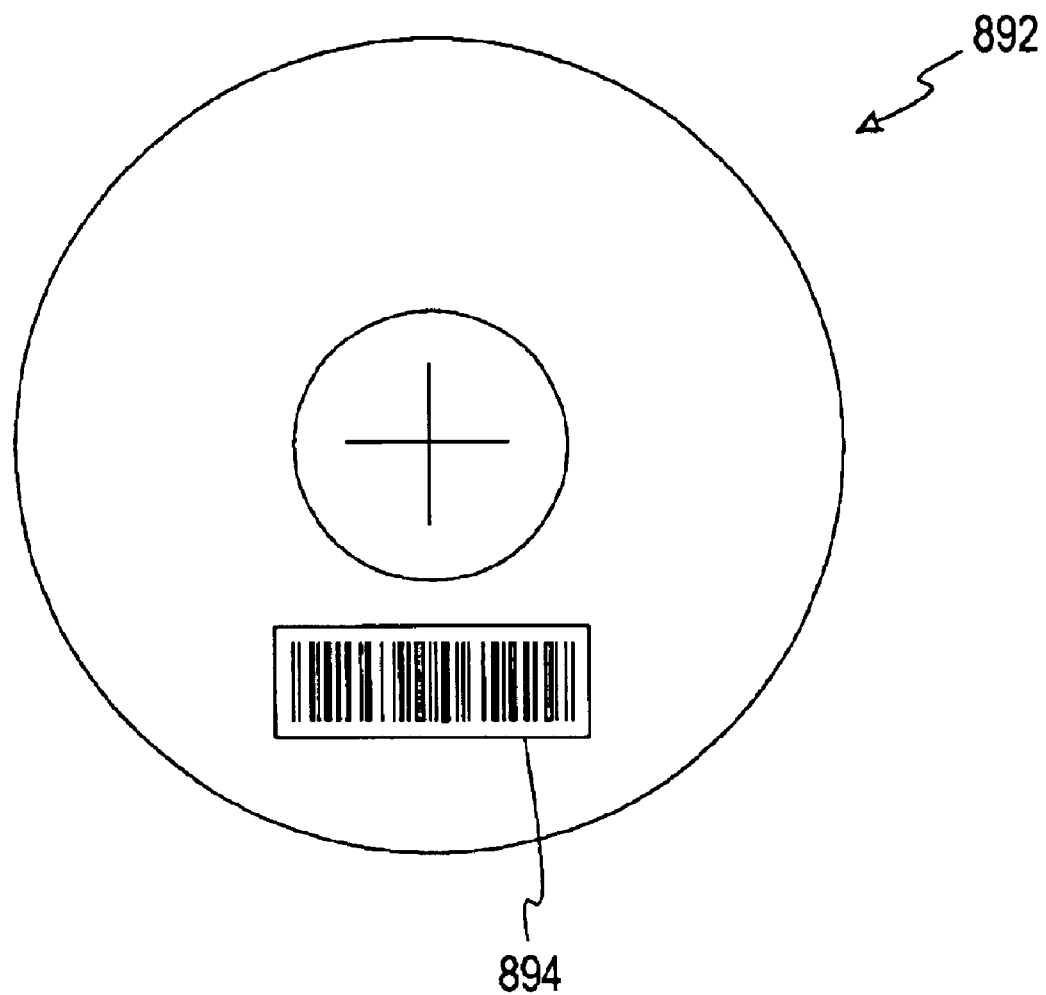
FIG. 9q is a top view of a healing abutment having a bar code information marker.

In addition to the markers described, it is further possible to provide a bar-coded system for providing information about the particular component as show in FIG. 9*q*. The bar code 894 can be located on the top surface on the healing abutment 892 such that it can be scanned or read easily. Thus, the bar code 894 would provide the same type of information described above with respect to the information markers.

Figure 10:
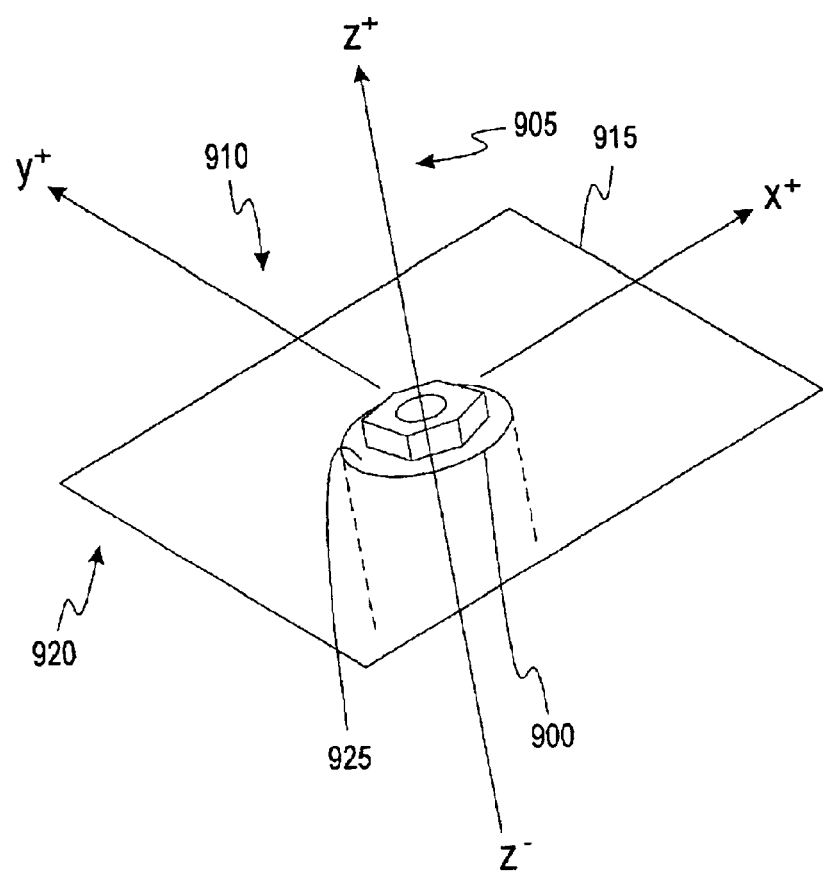
FIG. 10 is a perspective view of a coordinate system of one embodiment of the present invention.

Referring to FIG. 10, when scanning techniques are used to learn of the information on the top of the healing abutment, the computer software is able to determine the position and orientation of the implant 900 relative to the adjacent teeth. The position of the implant 900 is defined in a Cartesian coordinate system having "X," "Y," and "Z" axes. The common point is at the intersection of the centerline of the implant and a plane 920 representing the seating surface 925 of the implant 900.

As noted above, the information markers assist in determining the height of the healing abutment above the implant. This height can be used to identify the zero point on the "Z" axis, which is in the plane 920 containing the seating surface 925 of the implant 900. The "Y" axis 910 is within the plane 920 representing the seating surface 925 with the positive "Y" direction as close to the direction of facial to buccal as possible. The "X" axis 915 is in the plane 920 and is perpendicular to an implant hex face. Thus, the width of the seating surface 925 in the plane 920 is known, as is the width of the healing abutment emerging through the gingiva. Thus, the emergence profile of the artificial tooth is known, as well.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the present invention, which is set forth in the claims that follow.

What is claimed is:

1. A gingival healing abutment for attachment to a dental implant in combination with a scanning system, said healing abutment comprising:
at least three marking locations at known positions relative to each other at which identifying features may be present, a sequential combination of said identifying features from said at least three marking locations defining a code for said gingival healing abutment, said code indicating at least two characteristics of said healing abutment, said identifying features include grooves for creating protrusions in impression material, said impression material for making a model having replicating grooves that substantially replicate said grooves, said scanning system scans said replicating grooves in said model to acquire said code.

2. The healing abutment of claim 1, wherein said at least two characteristics include a height of said healing abutment and a diameter of a seating surface of said healing abutment.

3. The healing abutment of claim 1, further including a reference marker for identifying the order in which said identifying features are read for creating said sequential combination.

4. The healing abutment of claim 1, wherein said code is a binary code that includes one binary digit for each of said at least three marking locations.

5. The healing abutment of claim 1, wherein said healing abutment further comprises a fitting orientation marker for determining an orientation of a fitting of said healing abutment.

6. The healing abutment of claim 1, wherein said identifying features are four in number and said code is a binary code with four binary digits, said identifying features being a presence of a physical structure in said marking location that represents a "1" in said binary code or an absence of a physical structure in said marking location that represents a "0" in said binary code.

7. A gingival healing abutment for attachment to a dental implant in combination with a scanning system, said healing abutment comprising:
at least three marking locations at known positions relative to each other at which identifying features may be present, a sequential combination of said identifying features from said at least three marking locations defining a code for said gingival healing abutment, said code indicating at least two characteristics of said healing abutment, said identifying features include grooves for creating protrusions in impression material, said impression material for making a model having replicating grooves that substantially replicate said grooves, said scanning system scans protrusions in said impression material to acquire said code.

8. A gingival healing abutment for attachment to a dental implant in combination with a scanning system, said healing abutment comprising:
at least three marking locations at known positions relative to each other at which identifying features may be present, a sequential combination of said identifying features from said at least three marking locations defining a code for said gingival healing abutment, said code indicating at least two characteristics of said healing abutment, said scanning system scans said healing abutment for said identifying features to acquire said code.

9. A set of healing abutments, each of said healing abutments having unique characteristics and a plurality of marking locations, each of said plurality of marking locations providing a binary digit, said unique characteristics of each of said healing abutments being identifiable through a binary code that includes said binary digits from said plurality of marking locations.

10. The set of claim 9, wherein said unique characteristics include a height of said healing abutment.

11. The set of claim 9, wherein said unique characteristics include a diameter of the seating surface of said healing abutment.

12. The set of claim 9, wherein said binary digits are a "1" and a "0."

13. The set of claim 12, wherein said binary digit of "1" is a physical marking on said healing abutment at a certain location.

14. The set of claim 13, wherein said binary digit of "0" is an absence of a physical marking on said healing abutment at a certain location.

15. The set of claim 9, wherein said binary code includes four binary digits.

16. The set of claim 9, wherein said marking locations include a marker that is capable of developing a physical feature in impression material when said binary digit is "1."

17. The set of claim 16, wherein said marker is a groove.

18. The set of claim 16, said marker is a protrusion.

19. A method of developing a prosthetic tooth, said method comprising:

installing a dental implant into a jawbone;
attaching a gingival healing abutment to said dental implant, said gingival healing abutment having binary-coded markers for identifying physical characteristics of said gingival healing abutment;
determining said binary-coded markers to gather information for manufacturing said prosthetic tooth; and
developing a prosthetic tooth based on said information.

20. The method of claim 19, wherein said information includes a size of a seating surface of said implant.

21. The method of claim 19, wherein said information includes a location of said seating surface of said implant.

22. The method of claim 19, further including determining an orientation of a fitting of said implant.

23. The method of claim 22, wherein said determining said orientation includes analyzing a reference marker on said healing abutment.

24. The method of claim 19, wherein said developing said prosthetic tooth includes taking an impression of the region adjacent to said implant while said healing abutment remains on said implant, said binary-coded markers create features in said impression.

25. The method of claim 19, wherein said determining said binary-coded markers includes:

taking an impression of the region adjacent to said implant, said binary-coded markers creating features in said impression; and scanning said impression.

26. The method of claim 19, wherein said determining said binary-coded markers includes:

taking an impression of the region adjacent to said implant, said binary-coded markers creating features in said impression;

making a model of said impression; and scanning said model.

27. A method of collecting information useful for developing the subgingival regions of a prosthetic tooth, said method comprising:

attaching a gingival healing abutment to a dental implant, said gingival healing abutment having binary-coded markers on an outer surface;

taking an impression of the mouth region around said gingival healing abutment; and deriving said information from said binary-coded markers.

28. The method of claim 27, wherein said deriving said information occurs directly from a review of said binary-coded markers on said healing abutment.

29. The method of claim 27, wherein said binary-coded markers create features in said impression, said deriving includes reviewing said features in said impression.

30. The method of claim 27, wherein said binary-coded markers create features in said impression, and said method includes creating a model from said impression, said deriving includes reviewing said model.

31. A healing abutment for mounting on a dental implant, said healing abutment having a bar code providing information on at least a height and a diameter of said healing abutment, said information being used to develop a prosthetic tooth, said bar code being on an exterior surface that is positioned away from said dental implant.

* * * * *

UNITED STATES PATENT AND TRADEMARK OFFICE
CERTIFICATE OF CORRECTION

PATENT NO. : 6,790,040 B2
DATED : September 14, 2004
INVENTOR(S) : John T. Amber, Stephan S. Porter and Theodore M. Powell It is certified that error appears in the above-identified patent and that said Letters Patent is hereby corrected as shown below:

Title page,
Item [56], References Cited, OTHER PUBLICATIONS, "no. 2 (Exhibit B)" reference, please delete "conponent" and insert -- component --;
"no. 3 (Exhibit C)" reference, please delete "DERLIN™" and insert -- DELRIN™ --;
"no. 9 ("Managing The Soft Tissue Margin...") reference, please delete "Denistry," and insert -- Dentistry --.

Column 14,
Line 10, after "scans" insert -- said --;
Line 50, after "16," insert -- wherein --.

Signed and Sealed this

Twelfth Day of July, 2005

JON W. DUDAS
*Director of the United States Patent and Trademark Office*